(12) United States Patent
Stevens et al.

(10) Patent No.: US 8,216,203 B2
(45) Date of Patent: Jul. 10, 2012

(54) PROGRESSIVELY FUNCTIONAL STRETCH GARMENTS

(75) Inventors: Robert Alan Stevens, Menasha, WI (US); Christopher Peter Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2087 days.

(21) Appl. No.: 10/334,527

(22) Filed: Jan. 1, 2003

(65) Prior Publication Data

US 2004/0127881 A1    Jul. 1, 2004

(51) Int. Cl.
*A61F 13/15* (2006.01)
*A61F 13/20* (2006.01)

(52) U.S. Cl. .................................. 604/385.22

(58) Field of Classification Search ............. 604/385.22, 604/385.27, 394, 396
See application file for complete search history.

(56) References Cited

U.S. PATENT DOCUMENTS

| | | |
|---|---|---|
| 2,538,596 A | 1/1951 | Sheridan |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 4,041,203 A | 8/1977 | Brock et al. |
| 4,100,324 A | 7/1978 | Anderson et al. |
| 4,340,563 A | 7/1982 | Appel et al. |
| 4,355,425 A | 10/1982 | Jones et al. |
| 4,374,888 A | 2/1983 | Bornslaeger |
| 4,375,448 A | 3/1983 | Appel et al. |
| 4,494,278 A | 1/1985 | Kroyer et al. |
| 4,586,199 A | 5/1986 | Birring |
| 4,640,810 A | 2/1987 | Laursen et al. |
| 4,655,760 A | 4/1987 | Morman et al. |
| 4,657,802 A | 4/1987 | Morman |
| 4,663,220 A | 5/1987 | Wisneski et al. |
| 4,701,171 A | 10/1987 | Boland et al. |
| 4,701,175 A | 10/1987 | Boland et al. |
| 4,704,114 A | 11/1987 | Wilson et al. |
| 4,720,415 A | 1/1988 | Vander Wielen et al. |
| 4,747,846 A | 5/1988 | Boland et al. |
| 4,756,709 A | 7/1988 | Stevens |
| 4,770,656 A | 9/1988 | Proxmire et al. |
| 4,781,966 A | 11/1988 | Taylor |
| 4,789,699 A | 12/1988 | Kieffer et al. |
| 4,808,176 A | 2/1989 | Kielpikowski |
| 4,818,464 A | 4/1989 | Lau |
| 4,834,736 A | 5/1989 | Boland et al. |
| 4,834,738 A | 5/1989 | Kielpikowski et al. |

(Continued)

FOREIGN PATENT DOCUMENTS

EP    0 323 634    7/1989

(Continued)

*Primary Examiner* — Melanie Hand
(74) *Attorney, Agent, or Firm* — Dority & Manning, P.A.

(57) ABSTRACT

A pant-like absorbent article, such as a child's training pant, includes an outercover with at least three elastic regions, that is two in the side seam areas, and one in the central crotch areas. In an alternative, such articles include a fourth elastic region in the article waist band area. In this fashion, the article can demonstrate progressive stretch functionality to help accommodate various consumer body sizes and provide for more conforming fit and reduced leakage.

23 Claims, 4 Drawing Sheets

U.S. PATENT DOCUMENTS

| | | | |
|---|---|---|---|
| 4,842,596 A | 6/1989 | Kielpikowski et al. | |
| 4,872,871 A | 10/1989 | Proxmire et al. | |
| 4,923,456 A | 5/1990 | Proxmire | |
| 4,936,840 A | 6/1990 | Proxmire | |
| 4,938,753 A | 7/1990 | Van Gompel et al. | |
| 4,938,757 A | 7/1990 | Van Gompel et al. | |
| 4,940,464 A | 7/1990 | Van Gompel et al. | |
| 4,965,122 A | 10/1990 | Morman | |
| 4,981,747 A | 1/1991 | Morman | |
| 5,046,272 A | 9/1991 | Vogt et al. | |
| 5,057,368 A | 10/1991 | Largman et al. | |
| 5,069,970 A | 12/1991 | Largman et al. | |
| 5,104,116 A | 4/1992 | Pohjola | |
| 5,171,239 A | 12/1992 | Igaue et al. | |
| 5,178,931 A | 1/1993 | Perkins et al. | |
| 5,188,627 A | 2/1993 | Igaue et al. | |
| 5,188,885 A | 2/1993 | Timmons et al. | |
| 5,224,405 A | 7/1993 | Pohjola | |
| 5,226,992 A * | 7/1993 | Morman | 156/62.4 |
| 5,236,430 A * | 8/1993 | Bridges | 604/396 |
| 5,272,236 A | 12/1993 | Lai et al. | |
| 5,277,976 A | 1/1994 | Hogle et al. | |
| 5,284,703 A | 2/1994 | Everhart et al. | |
| 5,322,728 A | 6/1994 | Davey et al. | |
| 5,336,545 A | 8/1994 | Morman | |
| 5,340,424 A | 8/1994 | Matsushita | |
| 5,350,624 A | 9/1994 | Georger et al. | |
| 5,385,775 A | 1/1995 | Wright | |
| 5,440,764 A | 8/1995 | Matsushita | |
| 5,466,410 A | 11/1995 | Hills | |
| 5,486,166 A | 1/1996 | Bishop et al. | |
| 5,490,846 A | 2/1996 | Ellis et al. | |
| 5,527,171 A | 6/1996 | Soerensen | |
| 5,569,234 A | 10/1996 | Buell et al. | |
| 5,571,619 A | 11/1996 | McAlpin et al. | |
| 5,601,547 A | 2/1997 | Kato et al. | |
| 5,711,832 A | 1/1998 | Glaug et al. | |
| 5,746,731 A | 5/1998 | Hisada | |
| 5,749,865 A | 5/1998 | Yamamoto et al. | |
| 5,749,866 A | 5/1998 | Roe et al. | |
| 5,807,371 A | 9/1998 | Toyoda et al. | |
| 5,820,973 A | 10/1998 | Dodge, II et al. | |
| 5,827,260 A | 10/1998 | Suzuki et al. | |
| 5,843,068 A | 12/1998 | Allen et al. | |
| 5,846,232 A | 12/1998 | Serbiak et al. | |
| 6,059,764 A * | 5/2000 | Osborn et al. | 604/385.22 |
| 6,187,425 B1 | 2/2001 | Bell et al. | |
| 6,231,557 B1 | 5/2001 | Krautkramer et al. | |
| 6,336,921 B1 | 1/2002 | Kato et al. | |
| 6,358,350 B1 | 3/2002 | Glaug et al. | |
| 6,632,212 B1 * | 10/2003 | Morman et al. | 604/385.22 |
| 6,869,424 B1 * | 3/2005 | Morman et al. | 604/396 |
| 2002/0104608 A1 | 8/2002 | Welch et al. | |
| 2002/0123538 A1 | 9/2002 | Zhou et al. | |
| 2002/0183712 A1 | 12/2002 | Datta et al. | |

FOREIGN PATENT DOCUMENTS

| | | |
|---|---|---|
| EP | 0 217 032 | 2/1992 |
| EP | 0 320 989 | 4/1994 |
| EP | 0 753 292 | 1/1997 |
| EP | 0 761 193 | 3/1997 |
| EP | 0 587 196 | 3/1999 |
| WO | WO 00/35395 | 6/2000 |
| WO | WO 00/37009 | 6/2000 |
| WO | WO 00/47152 | 8/2000 |
| WO | WO 0047152 A1 * | 8/2000 |
| WO | WO 02/34185 | 5/2002 |
| WO | WO 02/41816 | 5/2002 |

* cited by examiner

PROGRESSIVELY FUNCTIONAL STRETCH GARMENTS

TECHNICAL FIELD OF THE INVENTION

The present invention relates generally to the field of absorbent articles and garments, such as disposable diapers, child's training pants, disposable swimwear, menstrual panties, incontinence articles, and the like, which incorporate stretch materials into their structure.

BACKGROUND

Many types of consumer care products such as disposable diapers, training pants, feminine care articles, incontinence articles, and the like, utilize an absorbent structure (retention layer) for absorbing and wicking away bodily fluids and other exudates, in combination with an elastomeric structure to achieve a form fitting garment-like product. The absorbent structures are conventionally formed from an absorbent web, typically a non-woven fibrous web material formed by known techniques which is disposed between a liquid pervious topsheet or bodyside liner layer and a liquid impermeable backsheet or outercover layer. In certain applications, portions of the liquid impermeable outercover are elastomeric to achieve some level of comfort while such articles are being worn. Such absorbent articles may also include an elasticized waistband and leg cuffs to help reduce the leakage of body exudates and to further provide improved fit to the consumer. Some conventional absorbent articles have also included elasticized containment or barrier flaps at the leg or waist sections of the article to further reduce the occurrence of leaks.

Conventional pant-like absorbent structures, such as a child's training pant, have also incorporated stretchable portions along their sides such as in the garment hip areas. Reference is made, for example, to the HUGGIES PULL-UPS disposable training pants from Kimberly-Clark Corporation of Neenah, Wis. The use of such elastomeric side panels in training pants is also described, for example, in U.S. Pat. No. 4,940,464 and WO 037009 which are incorporated by reference hereto in their entirety. Such conventional training pants include elastomeric side panels that are joined at side seams extending between a waist opening and respective leg openings. The seams may be permanent wherein the article is pulled onto the wearer in a manner similar to underwear. Alternatively, the seams may be releasable wherein the article may be put on and/or taken off similarly to a disposable diaper. However, with either of these types of configurations, it is not uncommon for the articles to include higher performance, and consequently more expensive, elastomeric materials in the sideseam areas, waist areas, and leg cuff areas, but with no or minimal elastomeric functionality elsewhere on the garment. For instance, it is not uncommon for absorbent articles with elastomeric materials to include LYCRA or other similarly pre-formed elastomeric film, band-like materials or ribbon-like structures in the waist and leg cuff areas, that are either sewn into or otherwise applied to the openings of the absorbent article, in order to provide some resistance against garment sagging and to assist in containing leaks. Furthermore, such materials may also include extruded high performance elastomeric materials, such as styrenic block copolymer materials sold under the brand KRATON, which usage also adds significant costs to the final consumer of such absorbent article products.

While the targeted placement of such higher performance elastomeric materials in the side, waist, and leg cuff areas addresses the need to provide articles with snug fit, and leak protection, it is often while sacrificing an elastic/conforming fit in the rest of the article. Consumers often have to rely on various pre-sized articles to accommodate changes/differences in user body size. Often, after such an article has been donned, it may lose some of its "tightness", and demonstrate sagging with continued use over time. This may be especially evident following a wearer insult (voiding) in the article, since the acts of donning, body movement and voiding in the article create additional load demands on the article over time.

In order to accommodate the various body sizes and shapes of consumers, such as children and adults who use such products, it would be desirable to have an article that could accommodate the needs of many individuals, without having to increase or significantly increase the cost of such products to the consumers. Such products would need to provide for enhanced fit around most of, or the entire article (circumferentially), as well as provide for the typical over-extension of such products at the waist, as routinely occurs when individuals donning such products pull such products over their legs and around their waistlines. Finally such products should be constructed so as to handle the additional load demands placed on the articles following article insult.

There is therefore a need for an absorbent article which provides full circumferential stretch around the body of the wearer using the article, without solely depending on expensive elastomeric materials to achieve this objective. There is further a need for a single absorbent article which can accommodate the many size needs of consumers, while still providing for the over-extension necessary for donning such products. It is to the foregoing needs that the current invention is directed.

SUMMARY OF THE INVENTION

An absorbent article includes a stretchable outercover layer, a liner layer, and an absorbent layer contained between the stretchable outercover layer and the liner layer, the absorbent article having a longitudinal direction and longitudinal ends, and a lateral direction and lateral sides. The article further includes a front waist region at a first longitudinal end, a back waist region at an opposite longitudinal end, and a crotch region extending longitudinally between the front and back waist regions. Laterally extending ear portions are defined at opposed lateral sides of the front and back waist regions. The outercover includes at least three material zones, with a first zone situated in the crotch region between the front waist region and the back waist region and demonstrating a level of hysteresis of between about 5 and 85 percent. Second and third zones are situated on the laterally extending ear portions of the outercover and demonstrate a level of hysteresis of between about 0 and 60 percent. In an alternative embodiment, the absorbent article includes a fourth zone situated at the front and back waist regions. The fourth zone demonstrates a level of hysteresis of between about 0 and 60 percent.

In a further alternative embodiment, an absorbent garment includes an absorbent chassis defining a waist opening and first and second leg openings; the absorbent chassis having a front region, a crotch region, and a back region, with two side panels each joining the front region and the back region, each of the side panels including a front panel and a back panel attached to one another along a side seam with an elastic waistband structure attached to the waist opening edge. The front, back and crotch regions are covered by an outer cover and the outer cover has a hysteresis of greater than or equal to 40% and a tension at 25% elongation (on a first extension cycle) of 300 g or more. The side panels have a hysteresis of less than or equal to 60% and a tension at 25% elongation (on a first extension cycle) of 100 g or more. The side waistband has a hysteresis of less than or equal to 60% and a tension at 25% elongation (on a first extension cycle) of 100 g or more.

In still a further alternative embodiment, an absorbent garment includes an absorbent chassis defining a waist opening and first and second leg openings; the absorbent chassis having a front region, a crotch region, and a back region, with two side panels each joining the front region and the back region, each of the side panels including a front panel and a back panel attached to one another along a side seam with an elastic waistband structure attached to the waist opening edge. The front, back and crotch regions are covered by an outer cover and the outer cover has a hysteresis of greater than or equal to 80% and a tension at 25% elongation (on a first extension cycle) of 400 g or more. The side panels have a hysteresis of less than or equal to 40% and a tension at 25% elongation (on a first extension cycle) of 200 g or more. The side waistband has a hysteresis of less than or equal to 40% and a tension at 25% elongation (on a first extension cycle) of 200 g or more.

In still a further alternative embodiment an absorbent garment includes an absorbent chassis defining a waist opening and first and second leg openings; the absorbent chassis having a front region, a crotch region, and a back region, with two side panels each joining the front region and the back region, each of the side panels including a front panel and a back panel attached to one another along a side seam with an elastic waistband structure attached to the waist opening edge. The front, back and crotch regions are covered by an outer cover and the outer cover has a hysteresis of between about 80% and 100% and a tension at 25% elongation (on a first extension cycle) of 500 g or more. The side panels have a hysteresis of less than or equal to 20% and a tension at 25% elongation (on a first extension cycle) of 250 g or more. The side waistband has a hysteresis of less than or equal to 20% and a tension at 25% elongation (on a first extension cycle) of 250 g or more.

Aspects of the invention will be described below in greater detail with reference to embodiments shown in the figures.

DETAILED DESCRIPTION

Figure 1:
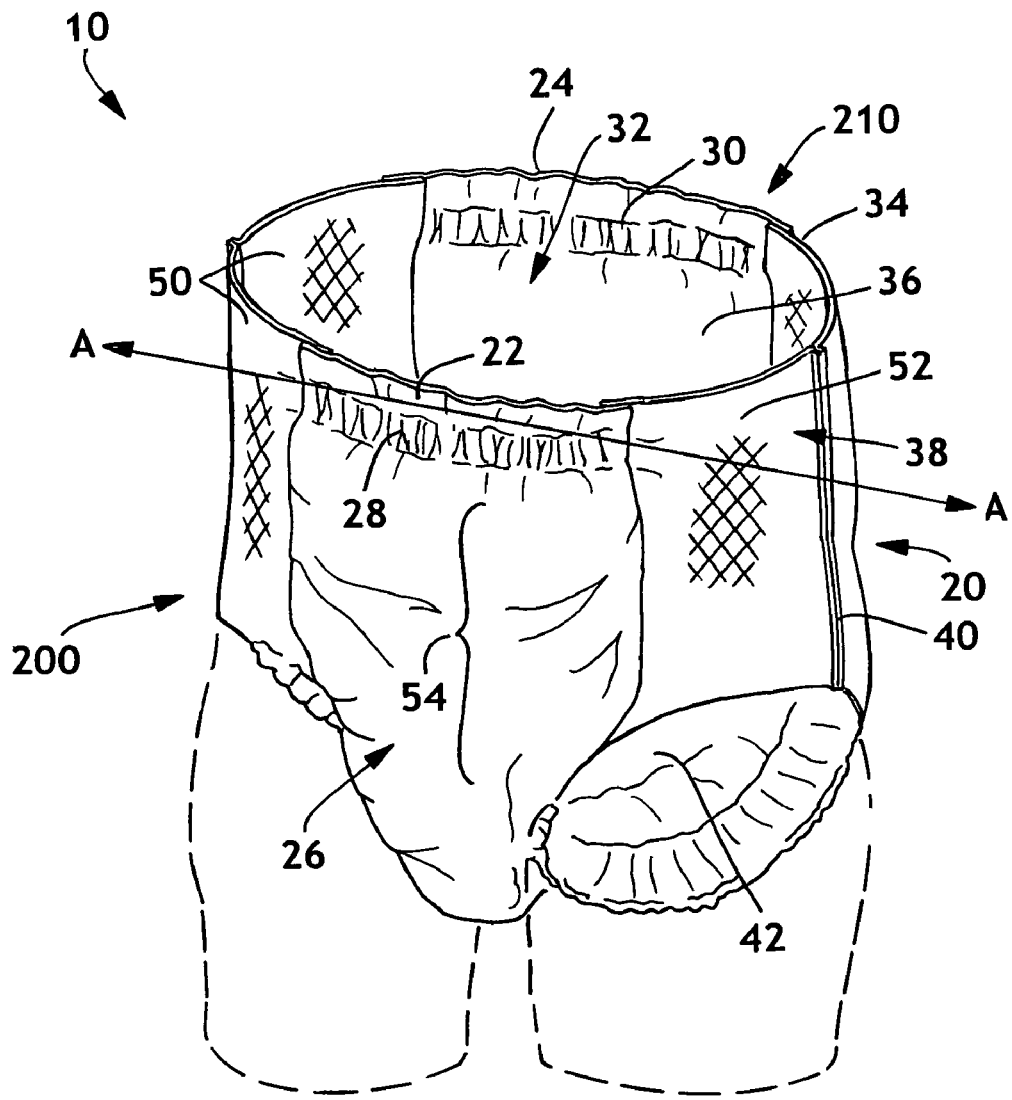
FIG. 1 is a front perspective view of a representative absorbent article (product) chassis, in this case a child's training pant, seen around a child's torso and upper legs, which are shown in phantom.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

DEFINITIONS

Within the context of the present description, the following terms shall have the following meanings:

As used herein, the term "absorbent article" shall be synonymous with "personal care product" and shall mean diapers, training pants, absorbent underpants, adult incontinence products, bandages and feminine care/hygiene products, such as for instance feminine care pads and pantiliners.

As used herein, the term "Airlaying" shall have the same meaning as "airlaid" and is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive. The absorbent composites of this invention may be made using the airlaid process. The production of airlaid nonwoven composites is well defined in the literature and documented in the art. Examples include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 Appel et al assigned to Kimberly-Clark Corporation, or other similar methods. Each of the foregoing patents is hereby incorporated by reference in its entirety. It should be understood that absorbent composites of this invention may, but need not be made using an airlaid process. For instance, the absorbent materials may also be fluff pulp and superabsorbent mixtures and various combinations.

"Attached" refers to the bonding, joining, adhering, connecting, attaching, or the like, of two elements. Two elements will be considered to be attached together when they are bonded directly to one another or indirectly to one another, such as when each is directly attached to an intermediate element.

As used herein, the term "bonded carded web" refers to webs that are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

As used herein, the term "breathable" refers to a material which is permeable to water vapor having a minimum WVTR (water vapor transmission rate) of about 500 g/m²/24 hours. The WVTR of a fabric, in one aspect, gives an indication of how comfortable a fabric would be to wear. WVTR is measured as indicated below and the results are reported in grams/square meter/24 hours. However, often applications of breathable barriers desirably have higher WVTRs and breathable barriers of the present invention can have WVTRs exceeding about 1,200 g/m²/24 hours, 1,500 g/m²/24 hours, 1,800 g/m²/24 hours or even exceeding 2,000 g/m²/24 hours.

As used herein, the term "coform" means a process in which at least one meltblown diehead is arranged near a chute through which other materials are added to the web while it is forming. Such other materials may be pulp (or fluff pulp), superabsorbent particles, cellulose or staple fibers, for example. Coform processes are shown in commonly assigned U.S. Pat. Nos. 4,818,464 to Lau and 4,100,324 to Anderson et al. each incorporated by reference in its entirety. Such process may also include multiple streams of different types of materials such as superabsorbent materials and fluff.

As used herein and in the claims, the term "comprising" is inclusive or open-ended and does not exclude additional unrecited elements, compositional components, or method steps.

"Elastomeric" refers to a material or composite which can be stretched or elongated by at least 25% of its relaxed length in at least one direction calculated as described below, and which will recover, upon release of the applied force, at least 10% of its elongation. It is generally preferred that the elastomeric material or composite be capable of being elongated by at least 100%, more desirably by at least 300%, of its relaxed length and recover at least 30% and more desirably 50% of its elongation upon release of a stretching, biasing force, within about one minute. An elastomeric material may thus be described as stretchable and "stretchy".

For the purposes of this application the terms "stretchy", "stretchable", "extensible", "elongatable" and "stretch" may be used interchangeably and shall describe a material function/attribute in which a given material is capable of elongating/extending or stretching in at least one direction a certain elongation, upon application of a biasing force (for instance, a biasing force in a range of 80 to 800 g per linear cm). For instance, an extensible material can be stretched without breaking by at least 25% (to at least 125% of its initial unstretched length) in at least one direction, suitably by at least 50% (to at least 150% of its initial unstretched length), more suitably by at least 100% (to at least 200% of its initial unstretched length). As an example, an extensible material having an initial unstretched length of 3 inches (7.6 centimeters) may be stretched without breaking to at stretched length of at least 3.75 inches (9.5 centimeters) in at least one direction (for the "by at least 25%" value). The terms encompass elastic/elastomeric materials as well as materials that stretch but do not significantly retract (that is do not significantly recover upon being stretched and released) such as, for example, necked nonwoven materials and inherently extensible nonwoven materials like bonded carded webs. While many of the embodiments described herein include stretchable components, it is also desirable in alternative embodiments that such stretchable components be elastic and elastomeric as well.

"Elastic" or "Elasticized" means that property of a material or composite by virtue of which it tends to recover some size and shape after removal of a force causing a deformation.

An "elastomer" is an elastic-like polymer. A "plastomer" is an extendable polymer. Polymers which are capable of stretching several times their original dimension when a force is applied and then quickly recover or regain the original dimension or nearly the original dimension when the force is removed are known to exhibit rubber elastic behavior. Polymers which are capable of deformation under the influence of a force but have little or no tendency to regain shape upon the removal of the force are plastic-like. Plastomers are neither fully elastic nor plastic but show varying degree of elasticity and plasticity under given conditions. Hence, some of their properties, for instance stress-elongation, may appear to be elastic. A plastomer may show 1000%, or 800% or 600% elongation at break. It may give low modulus in the range of 1000 to 7000 psi. However, for certain characteristics such as hysteresis and tension set, as the elongation becomes higher and higher, a plastomer will show plastic like behavior with a high percentage set and hysteresis while an elastomer in a similar condition gives a low percentage set, and hysteresis. For the purposes of this application, a high or higher performance elastomer shall demonstrate lower hysteresis than a lower performance elastomer, a stretchable material or plastomer and desirably between about 0 and 40 percent. Also for the purposes of this application, a low or lower performance elastomer, stretchable material or plastomer will demonstrate higher hysteresis than a higher performance elastomer and desirably between about 40 and 100 percent.

As used herein, the term "garment" means any type of apparel which may be worn. This includes industrial work wear and coveralls, undergarments, pants, shirts, jackets, gloves, socks, absorbent articles and the like.

The term "insult" refers both to the natural deposition of a body exudate, and in particular urine voids or menses liquids during absorbent product use by a wearer, as well as the deposition of simulated body exudates during absorbent product testing.

The term "load" or "loads" shall mean the force used on a sample or garment to generate a stress strain curve or alternatively, the force imposed on a sample or garment during use.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface. The foregoing patent is hereby incorporated by reference in its entirety.

As used herein, the term "machine direction" or MD means the length of a fabric in the direction in which it is produced. The term "cross direction" or "cross machine direction" or CD means the width of fabric, i.e. a direction generally perpendicular to the MD.

"Member" when used in the singular can refer to a single element or a plurality of elements.

As used herein "multilayer nonwoven laminate" means a laminate of two or more layers in which at least one of the layers is a nonwoven material such as, for instance, a spunbond layer. For example, a multilayer nonwoven laminate may include a spunbond/meltblown/spunbond (SMS) laminate, or a laminate in which at least one of the layers is a nonwoven and the other layer(s) is another material such as a film in a spunbond/film laminate (SF). Examples of multi-layer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. each being incorporated by reference in its entirety. Such a laminate may be made by for example, sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein, the term "necked material" refers to any material which has been constricted in at least one dimension by processes such as for example, drawing or gathering.

As used herein, the term "neckable material" refers to any material which can be necked. See for instance U.S. Pat. No. 4,965,122 which is incorporated herein in its entirety by reference hereto.

"Neck-bonded" laminate refers to a composite material having an elastic member that is bonded to a non-elastic member while the non-elastic member is extended in the machine direction creating a laminate that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "percent stretch" refers to the ratio determined by measuring the increase in the stretched dimension and dividing that value by the original dimension. i.e. (increase in stretched dimension/original dimension)×100.

As used herein, the term "personal care product" shall mean diapers, training pants, absorbent underpants, adult incontinence products, bandages and feminine care/hygiene products.

As used herein the term "set" refers to retained elongation in a material sample following the elongation and recovery in the first cycle of the Extension/Retraction Test described herein. Set as used herein has units of percent (%). The percent set or set is calculated as follows:

Set={(Gage length at zero load in the retraction cycle−the original sample length)/the original sample length}×100

As used herein the term "percent set" is the measure of the amount of the material stretched from its original length, such as after being cycled. The remaining strain after the removal of the applied stress is measured and reported as a percent set. The percent set is where the retraction curve of a cycle crosses the elongation axis, and as further discussed below. This term may encompass the term "permanent set".

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein the term "recover" refers to a contraction of a stretched material upon termination of a biasing force following stretching of the material by application of the biasing force. For example, if a material having a relaxed, unbiased length of 1 inch (2.5 cm) is elongated fifty percent by stretching to a length of 1.5 inches (3.75 cm), the material would have a stretched length that is 150 percent of its relaxed length or stretched 1.5×. If this exemplary stretched material contracted, that is recovered to a length of 1.1 inches (2.75 cm) after release of the biasing and stretching force, the material would have recovered 80 percent of its 0.5 inch (1.25 cm) elongation. Percent recovery may be expressed as [(maximum stretch length−final sample length)/(maximum stretch length−initial sample length)]×100. The unrecovered material elongation would be the set in the material.

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes. Each of the foregoing patents are hereby incorporated by reference in their entirety.

"Stretch-bonded" laminate (SBL) refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-elastic layer is fully extended. Examples of stretch-bonded laminates are disclosed, for example, in U.S. Pat. Nos. 4,720,415, 4,789,699, 4781,966, 4,657,802, 4,655,760, 5,385,775 and U.S. Patent Application No. US2002-0104608 which is incorporated herein by reference in its entirety for all purposes.

"Tension" refers to the stress within a body that opposes a force tending to cause the extension of a body, or to the balancing force within that body resisting the extension. Tension may be expressed in units of grams. The force tending to cause the extension is the load.

As used herein the term "thermal point bonding" involves passing a fabric or nonwoven web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "ultrasonic bonding" means a process performed, for example, by passing the fabric between a sonic horn and anvil roll as illustrated in U.S. Pat. No. 4,374,888 to Bornslaeger, incorporated by reference herein in its entirety.

As used herein, the terms "zones", "areas", "regions", and "portions" shall be used synonymously to mean a particular location along an article outercover or side panels that includes similar construction materials, such as a polymeric laminate of a particular type. For the purposes of this application the term zones, may refer to, but is not limited to, the side panel areas of an absorbent article, that is the area generally at the hips of the article, the central crotch area of an absorbent article, that is the area that is generally situated between the legs from the front waist to the rear waist, and the waist area of an absorbent article, that is the area that immediately surrounds the waist opening in an absorbent article.

Test Methods:

WVTR Test:

The water vapor transmission rate (WVTR) for sample materials may be calculated in accordance with the following test method. Circular samples measuring three inches in diameter should be cut from each of the test materials and a control which is a piece of CELGARD 2500 film from Hoechst Celanese Corporation of Sommerville, N.J. CELGARD 2500 film is a microporous polypropylene film. Three samples should be prepared for each material. The test dish is a number 60-1 Vapometer pan distributed by Thwing-Albert Instrument Company of Philadelphia, Pa. One hundred milliliters of water should be poured into each Vapometer pan and individual samples of the test materials and control material should be placed across the open tops of the individual pans. Screw-on flanges should be tightened to form a seal along the edges of the pan, leaving the associated test material or control material exposed to the ambient atmosphere over a 6.5 centimeter diameter circle having an exposed area of approximately 33.17 square centimeters. The pans should then be placed in a forced air oven at about 100° F. (38° C.) for 1 hour to equilibrate. The oven should be a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans should be removed from the oven, weighed and immediately returned to the oven. After 24 hours, the pans should be removed from the oven and weighed again. The preliminary test water vapor transmission rate values should be calculated with Equation (I) below:

$$\text{Test WVTR} = (\text{grams weight loss over 24 hours}) \times 315.5 \text{ g/m}^2/24 \text{ hours} \quad (I)$$

The relative humidity within the oven should not be specifically controlled.

Under the predetermined set conditions of about 100° F. (38° C.) and ambient relative humidity, the WVTR for the CELGARD 2500 control has been defined to be 5000 grams per square meter for 24 hours. Accordingly, the control sample should be run with each test and the preliminary test values should be corrected to set conditions using Equation (II) below:

$$\text{WVTR} = (\text{Test WVTR/control WVTR}) \times (5000 \text{ g/m}^2/24 \text{ hours}) \quad (II)$$

Extension/Retraction Tests:

(Procedure for Determining Stretch Characteristics)

This procedure is a single-cycle bench test to measure the stretch characteristics of a loop of stretchable material across a range of tensions. The test material is cycled to a specific loading rather than to a fixed elongation/tension. The generated values are used as a means to measure material functionality and to determine interactions between materials across a range of tensions.

The data generated by this test method includes circumference (mm) at an initial load of 70 g, and circumference (mm) at a final (peak) load of 2000 g, stress/strain curves for one full cycle of extension/retraction, and permanent set and hysteresis loss resulting from that cycle. If significant rupturing of bonds, fibers, film, etc. within the sample's materials or composite structure begins to occur at less than 2000 g, the maximum load is reduced to an amount that does not significantly damage the test sample.

Figure 6:
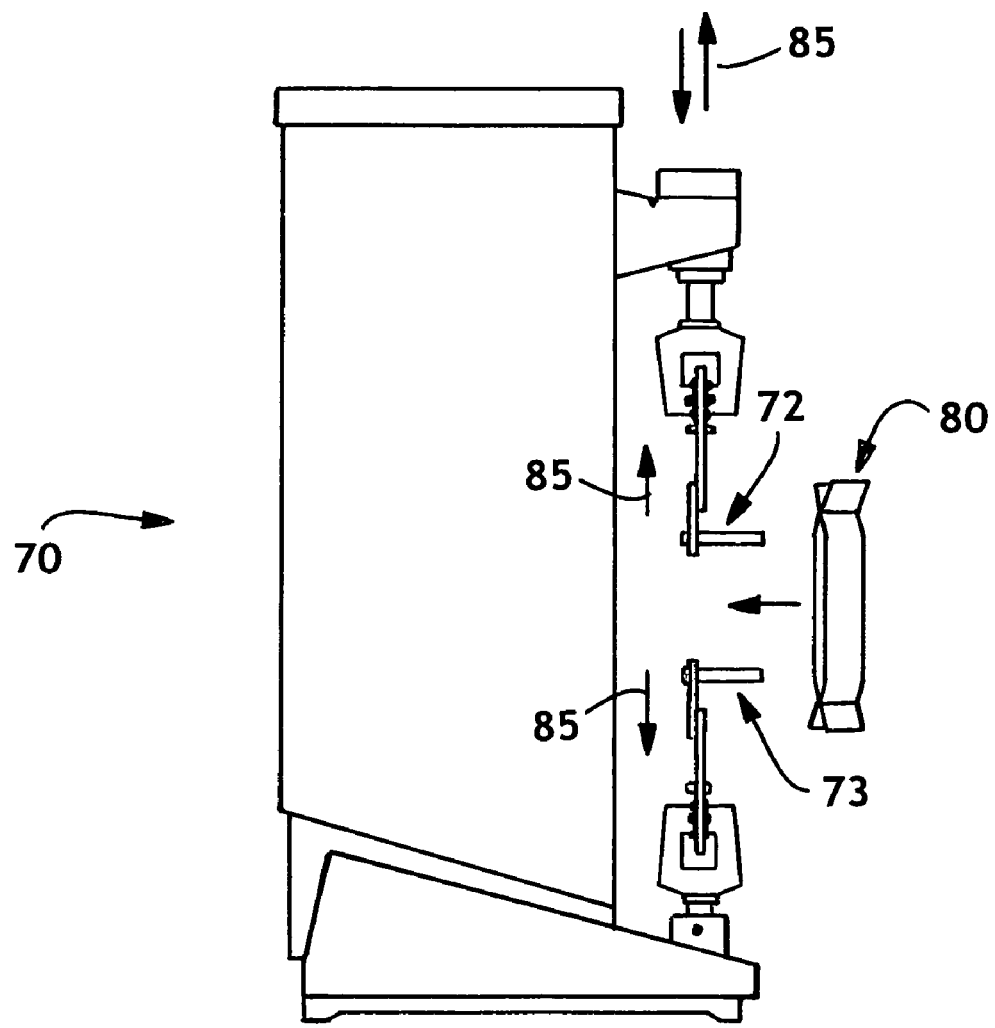
FIG. 6 represents a side view of an apparatus used for measuring material attributes as described in the application.

As can be seen in FIG. 6, an apparatus 70 for measuring such stresses is illustrated. A material loop 80 is suspended from the top pin 72 of a testing apparatus 70, with the bottom of the material loop hanging loosely around the bottom pin 73. When the test equipment is activated, the pins will separate (as indicated by arrows 85) until a force of 2000 g is reached, and then automatically return to the original starting position. Time, force and distance data is automatically recorded to generate the stress/strain (extension/retraction) curves.

At least three loops of each type of material are generally tested. A computer program is used to average specific points along the extension/retraction curve of each sample to produce a composite curve representing all individual test results.

Apparatus and Materials:
1) JDC Precision Sample Cutter, 1 inch wide, made by Thwing-Albert Instrument Co, Philadelphia, Pa.
2) Constant Rate of Extension (CRE) tensile tester; MTS tensile tester model Synergie 200 Test Bed; available from MTS Systems Corporation, Research Triangle Park, N.C. USA.
3) Load Cells: A suitable cell selected so the majority of peak load values fall between the manufacturer's recommended ranges of load cell's full scale value: Model 100N available from MTS Systems Corporation, Research Triangle Park, N.C., USA.
4) Operating Software and data Acquisition system: MTS Testworks for Windows software version 3.10; available from MTS Systems Corporation, Research Triangle Park, N.C. USA.
5) Grips: pneumatic-action grips, top and bottom, identified as part number 2712-003 available from Instron Corporation, Canton, Mass., USA.
6) Gripfaces: 25 by 75-mm (1 inch by 3 inch), suitable for holding pins.
7) Pins: rigid pins having a length of 6.3 centimeters (2.5 inch) and a knurled portion at one end for holding specimens, the knurled portion having an outside diameter of 6.4 millimeter (0.25 inch) and a length of 3.2 centimeters (1.25 inches).

Conditioning:

Reasonable ambient conditions should be used for sample testing, such as 73±2 degrees F. and a relative humidity of 50±2%. The instruments used should be calibrated as described in the manufacturer's instructions for each instrument.

Test Specimen:

The sample material is cut to 1 inch widths using the precision cutter. Two pieces are bonded together (desirably using an ultrasonic bonder to generate a strong bond such that they form a loop), with 160 mm between bonds and having a total circumference in the relaxed loop of 320 mm. For the purposes of this testing the bonding was accomplished with a Branson Model 920 Ultrasonic Plunge bonder, operating at 20,000 cycles/sec. The horn was ½ inch by 9 inches, and the anvil was ¼ inch by 7 inches with a dot embossing pattern engraved therein (about 225 dots per square inch). Bonding conditions were about a two second dwell time with 60 psi horn pressure. Bonds were permanent and stable. If bonds of sufficient strength cannot be formed through sonic bonding, alternate bonding methods may be used such as adhesives or stapling with a common office stapler or the like.

Procedure:

The Tensile Tester test conditions are as follows: The crosshead speed is 250 mm/min, the full scale load is 4540 g, the gage length is 10 mm shorter than the loop bond length, in this case 150 mm, the go to load (cycle trigger) is 2000 g, the number of cycles is 1, the elongation stop is 450 mm (200%) and the break sensitivity is 75%.

The load cell is calibrated using the Testworks software at the beginning of the session. The pin assemblies are installed as depicted in FIG. 6. Using the tensile frame pushbutton controls for crosshead position, the pins are moved to the required gage length. The gage length is determined by measuring from the centerline of the first pin to the centerline of the second pin. The software is calibrated to this initial gage length. The band is placed onto the knurled section of the top pin. The loop bottom of the material is beneath the bottom pin. "Zero" is clicked on to tare the load of the specimen. The "RUN" button is clicked on and the test will start automatically. When the test is done, either the "FILE" is clicked on to save the data and graphs or the "NEXT" is clicked on to save only the data. The specimen is removed from the pins. The steps are repeated (from placing the specimen on the pins) for each specimen until the testing for the sample population is complete.

Hysteresis is a measurement of the amount of energy loss within a specific cycle. The loading and unloading energy are calculated by integrating the area under the respective curves using the Trapezoidal rule. The percent hysteresis of a cycle is defined as:

$$\% \text{ Hysteresis} = \frac{\text{Loading Energy} - \text{Unloading Energy}}{\text{Loading Energy}} \times 100$$

"Stretch to Stop" Test:

The Stretch to Stop test is the elastic limit before the spunbond layer (or other nonelastic nonwoven) of an elastic material/spunbond (or other nonelastic nonwoven) laminate takes over the stress-elongation behavior. In the elongation at stop, or "stretch to stop" test, a 3 inch by 6 inch (76 mm by 152 mm) sample, with the larger dimension being the machine direction, is placed in the jaws of the Sintech 2 machine using a gap of 50 mm between the jaws. The sample is then pulled to a stop load of 2000 g (grams) with a crosshead speed of about 500 mm per minute. If significant rupturing of bonds, fibers, film, etc. within the sample's materials or composite structure begins to occur at less than 2000 g, the maximum load is reduced to an amount that does not significantly damage the test sample and the stretch to stop is calculated at this lower load. The elongation in percent, relative to the unstretched length at this point is the stretch to stop value. This number can be normalized for material samples of less width.

If a 76 mm wide sample is not available the test can still be run by normalizing the stop load to the width of the sample. For example, if the widest sample available was only 25 mm, the stop load would be normalized to 658 grams, thereby keeping the stop load per linear mm width constant.

If a full 152 mm long sample is not available, the test can still be run using the available sample length as the unstretched length in the calculation of the stretch to stop value. If less than 50 mm of length is available, the gap between the jaws can be reduced to the length of the available sample.

The elongation at stop test also yields the value for elongation at intercept. The elongation at intercept is the load in grams where the elasticity of the material ends and the tensile strength of the sample takes over.

Hydrohead Test:

A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. The hydrohead data for the purposes of this application may be obtained using a test method similar to the aforesaid Federal Test Standard except as modified and noted below. The hydrohead may be determined using a hydrostatic head tester available from Mario Enterprises, Inc. of Concord, N.C. The specimen may be subjected to a standardized water pressure (as opposed to a column of water as in the Federal Test Standard) which is increased at a constant rate until leakage appears on the surface of the fabric in three separate areas. (Leakage at the edge, adjacent to the clamps is ignored.) Unsupported fabrics, such as thin film, can be supported to prevent premature rupture of the specimen.

Various aspects and embodiments of the invention will be described in the context of a disposable absorbent article/garment, such as a child's training pant. It is, however, readily apparent that the present invention could also be employed with other articles, disposable diapers, feminine care articles, incontinence garments and the like. Typically, the disposable articles are intended for limited use and are not intended to be laundered or otherwise cleaned for reuse. A child's training pant, for example, is discarded after it has become soiled by the wearer. In its various aspects, the invention can provide a distinctive absorbent article which exhibits desirable physical properties, such as softness, flexibility, conformance, trim appearance, reduced gapping and reduced leakage. As a result, the absorbent articles of the invention can provide improved fit, and reduced clumping, bunching or sagging during use.

With reference to the figures, an article, such as that representatively shown as a child's training pant 10 in FIG. 1, includes a body or chassis 20 having a lengthwise, longitudinal direction Y (FIG. 2), a lateral, transverse cross-direction X (FIG. 2), a front waist region 22 on a front side 200, a back waist region 24 on a back side 210, and an intermediate crotch region 26 interconnecting the front and back waist regions. The waist regions including their (laterally extending flared side ear portions) 22 and 24 comprise those portions of the article 10 which when worn, wholly or partially cover or encircle the waist or mid-lower torso of the wearer. In particular configurations, the front 22 and back 24 waist regions may include elastic front and back side waistband portions 28, 30. The elastic waistband portions may either be generally continuous around the waist opening 32 of the article, or as illustrated, the waistband portions may extend only partially across their respective waist side regions. Additional elastic material for conforming the waist area, may be found in the side panels 50 and 52 which surround the hip areas of the garment. These side panel areas may be of separate material construction from the crotch, front and back waist materials.

The intermediate crotch region 26 lies between and interconnects the waist regions 22 and 24, and comprises that portion of the article 10 which, when worn, is positioned between the legs of the wearer and covers the lower torso of the wearer. Thus, the intermediate crotch region 26 is an area where repeated fluid and/or waste surges typically occur in the training pant or other disposable absorbent article when the wearer is in an upright position.

The article 10 includes a substantially liquid-impermeable outer cover member 34, a liquid-permeable bodyside liner 36, and an absorbent body structure (not shown) sandwiched between the outer cover member 34 and the bodyside liner layer 36, and generally positioned in the crotch area 26, so as to catch body waste as it enters the article. The absorbent body structure (also referred to as an absorbent layer or retention layer) may be secured to the outer cover member 34 by an adhesive, and secured to the bodyside liner 36 by an adhesive. In variations of the structure, the absorbent body structure need not be attached to either of the bodyside liner or the outercover, but may "float" between them, or may, alternatively be attached to only one of these layers.

In certain embodiments, a surge management layer not (shown) may be optionally located adjacent the absorbent structure, between the liner layer and the absorbent layer and attached by way of adhesive. A surge management layer helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference in their entirety for all purposes.

Figure 2:
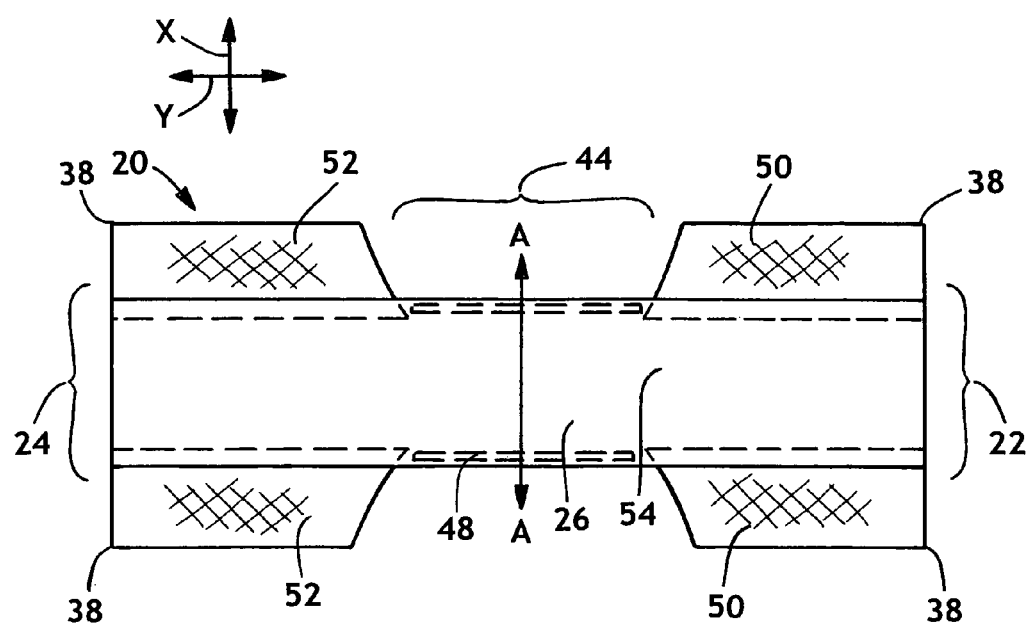
FIG. 2 is a simplified topside (bodyside) plan view of the absorbent article chassis of FIG. 1 in a flat out state (without the gathering normally associated in an article with elastomeric components).

The training pant 10 may be of a style and configuration wherein the front and back waist portions 22, 24 have lateral sides 38 (side panels) that are brought together upon folding the chassis to form a pant structure having the waist opening 32 and leg open 26 of the chassis 20 to define curved leg contours 44, as particularly seen in FIG. 2. Essentially, the two side panels each join the front and the back, with each of the side panels including a front panel and a back panel attached to one another along a side seam (or through a refastenable mechanism) and with an elastic waistband structure attached to the waist opening edge. The curved leg contours 44 define the leg openings 42 when the article is assembled. The article may be of a single piece construction or alternatively, the lateral sides 38 separate and then are bonded in a known manner so as to define side seams 40 of the pant structure. With either of these types of configuration, the pant 10 is pulled on by the wearer in a manner similar to underwear. Desirably, in one embodiment these seams 40 may be separable or tearable so that the pant 10 may be removed from the wearer by tearing the seams 40 and removing the article in a manner similar to a diaper. In an alternate embodiment, the front and back waist portions 22 and 24 may be separable and re-attachable (refastenable) at the side seams 40. A fastening system, such as a hook-and-loop system, or a refastenable tape system, may be used to interconnect the first waist region 22 with the second waist region 24 to define the pant structure and hold the article on a wearer. Additional suitable releasable fastening systems are described in U.S. Pat. No. 6,231,557 B1 and the International Application WO 00/35395, these references being incorporated herein by reference in their entirety for all purposes.

FIG. 2 shows a plan view of the representative training pant 10 in its generally flat-out, (i.e., with substantially all elastic induced gathering and contraction removed). In this view, the bodyside surface of the pant 10 which contacts the wearer is facing the viewer, and portions of the structure are partially shown in phantom to more clearly show the interior construction of the article. The outer edges of the article 10 define a periphery with longitudinally extending lateral sides and lateral sides 38. The longitudinal ends are shown as straight, but optionally, may be curvilinear. As mentioned, when the pant structure is formed by joining the lateral sides 38 of the front and back waist portions (after folding the article in a direction transverse to the longitudinal direction, such as along line A-A (of FIG. 1), the side contours 44 define leg openings for the article 42.

Elastomeric gathering members, such as leg elastics and waist elastics may be provided, as is well known in the art. The liner, absorbent structure, surge layer if present, and elastic gathering members may be assembled together into a variety of well-known absorbent article configurations.

The leg elastic members 48 may be located in the lateral side margins of the chassis 20, particularly along the lateral sides of the crotch region 26, and are configured to draw and hold the chassis 20 against the legs of the wearer. The elastic members 48 are secured to the chassis 20, for example with an adhesive, in an elastically contracted state so that in a normal under-strain condition, the elastic members 48 effectively contract against the chassis. The use of elastic leg members in absorbent articles such as disposable diapers and training pants is widely known and understood in the art.

The use of elastic waistbands is also widely known and used in the art. In the illustrated embodiment of FIG. 1, the waist elastics are provided across at least a portion of the front and back waistband areas 28 and 30. In alternate embodiments, the waist elastics may extend completely across the front and back waistbands. The waist elastics may be composed of any suitable elastomeric material, such as an elastomeric film, an elastic foam, multiple elastic strands, an elastomeric fabric, and the like. Embodiments of waistband structures that may be utilized with articles 10 according to the invention are also described in U.S. Pat. Nos. 5,601,547; 6,358,350 B1; 6,336,921 B1; and 5,711,832, incorporated by reference herein in their entirety for all purposes.

The liner 36 and outer cover member 34 may be generally coextensive, and may have length and width dimensions which are generally larger than and extend beyond the corresponding dimensions of the absorbent structure contained between them. The extending portions define the corresponding side and end margins that allow for the waistbands, leg elastics, and side seams used to attach together the outer cover member 34 and liner 36. Optionally, the bodyside liner and outer cover member may not be coextensive.

The outer cover member may be composed of a liquid permeable material, but desirably comprises a material which is configured to be substantially impermeable to liquids. For example, a typical outer cover can be manufactured from a thin plastic film, a composite laminate, or other flexible, substantially liquid-impermeable material.

Alternative constructions of the outer cover member may comprise a woven or non-woven fibrous web layer which has been totally or partially constructed or treated to impart the desired levels of liquid impermeability to selected regions that are adjacent or proximate the absorbent body structure. For example, the outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover typically provides the outermost layer of the article, optionally the article may include a separate outer cover component member which is additional to the outer cover member.

The outer cover may define the entire front and back waist regions. The outer cover may, for example, be composed of a single layer, multiple layers, laminates, spunbond fabrics, films, meltblown fabrics, netting, a microporous web, bonded carded webs or foam materials. Nonwoven laminate webs may include a nonwoven material joined to one or more gatherable nonwoven webs, films, or foams. Examples of suitable materials are Spunbond-Meltblown fabrics, Spunbond-Meltblown-Spunbond fabrics, Spunbond fabrics, or laminates of such fabrics with films, foams, continuous filament strands or other nonwoven webs. The outer cover may include materials that have demonstrated various properties through a mechanical process, printing process, heating process, or chemical treatment. For examples such materials may be apertured, creped, neck-stretched, heat activated, embossed, and micro-strained; and may be in the form of films, webs, and laminates.

The bodyside liner 36 presents a body-facing surface which is compliant, soft-feeling, and non-irritating to the wearer's skin. Further, the bodyside liner can be less hydrophilic than the absorbent body, and is sufficiently porous to be liquid permeable, permitting liquid to readily penetrate through its thickness to reach the absorbent body structure. A suitable bodyside liner layer 36 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner layer is typically employed to help isolate the wearer's skin from liquids held in the absorbent body.

Various woven and nonwoven fabrics can be used for the bodyside liner 36. For example, the bodyside liner may include a meltblown web, a spunbonded web, or a bonded-carded-web composed of the desired fibers. The various fabrics can be composed of natural fibers, synthetic fibers or combinations thereof. In particular aspects, the bodyside liner 36 may be comprised of polymer fibers, networks, laminates, liquid permeable films, cellulosic fibers, rayon, water swellable gels, and elastomeric materials, as well as combinations thereof. Suitable materials for the bodyside liner can include meltblown webs, airlaid webs, spunbond webs, or bonded-carded webs of synthetic continuous or discrete polymer fibers and/or natural fibers, a pattern bonded spunbonded web, airlaid web, or bonded carded web, as well as combinations thereof. Suitable polymers can include polypropylene, polyethylene, polyester, and bicomponent materials composed of these polyolefins.

The bodyside liner fabrics may be composed of a substantially hydrophobic material, and the hydrophobic material may optionally be treated with a surfactant or otherwise processed to impart a desired level of wettability and hydrophilicity. In a particular embodiment of the invention, the bodyside liner 36 can be a nonwoven, spunbond polypropylene fabric which is necked approximately 60%. Strands of KRATON G2760 elastomer material may be adhered to the necked spunbond material. The fabric can be surface treated with an operative amount of surfactant, such as about 0.45% AHCOVEL Base N62 surfactant, available from Uniqema, a division of ICI, a business having offices located in New Castle, Del. The surfactant can be applied by any conventional means, such as spraying, printing, brush coating or the like. The bodyside liner may or may not be elastomeric. If it is not elastomeric, it is desirably gatherable, such that it is larger in surface area than the outercover to which it is attached, and has room to expand if it is bonded to an elastomeric outercover, or alternatively is extensible, or further alternatively, is bonded in only limited locations to the outercover such that the bonds may easily rupture upon in-use extension of the outercover. In any event, it is desirable that such bodyside liner not interfere with elastomeric properties which may be demonstrated by the outercover.

In particular embodiments wherein it is desired that the bodyside liner layer 36 be stretchable, suitable elastomeric materials can include elastic strands, LYCRA® elastics, elastic films, cast or blown; nonwoven elastic webs, meltblown or spunbond elastomeric fibrous webs, as well as combinations thereof. Additionally, such stretchable liners can include stretchable bicomponent fibrous materials such as bicomponent sheath/core fibrous nonwoven fabric produced on a spunbonded process. In such a process, thermoplastic fibers or strands are extruded, quenched, drawn, and collected on a moving forming wire. The fibrous material then may be bonded at thermal bond points to induce some structural integrity. Bond points are typically formed in a heated calender and then the fabric wound onto a roll. The bond points of such materials could be Hansen Pennings, wire weave, and Expanded Hanson Pennings described above, for example.

The core of the bicomponent material may consist of thermoplastic rubber-like elastomeric materials, such as those which are available from Kraton Polymers of Houston, Tex. (styrenic block copolymers), or Affinity polymers from Dow Chemical (metallocene catalyzed PE) may be used. The sheath material can be an olefinic material such as thermoplastic polypropylene from Exxon, such as 3854 or 3445 or polyethylene from Dow such as 6811. Depending on their composition and forming process, such spunbond materials may have surface topographies to provide additional expansion of the material, in addition to the expansion of the fabric based on orienting the fibers during stretch.

Further examples of elastomeric materials for use in a liner material include HYTREL elastomers, ESTANE elastomeric polyurethanes (available from B.F. Goodrich and Company located in Cleveland, Ohio), or PEBAX elastomers. The bodyside liner may include blends or laminates of fibers, scrim, webs, and films with perforations, apertures, creping, heat activation, embossing, micro-straining, chemical treatment, or the like, as well as combinations thereof.

The bodyside liner 36 and outer cover 34 may be connected or otherwise associated together in an operable manner. As used herein, the term "associated" encompasses configurations in which the bodyside liner 36 is directly joined to the outer cover 34 by affixing the bodyside liner 36 directly to the outer cover 34, and configurations wherein the bodyside liner 36 is indirectly joined to the outer cover 34 by affixing the bodyside liner 36 to intermediate members which in turn are affixed to the outer cover 34. The bodyside liner 36 and outer cover 34 can, for example, be joined to each other in at least a portion of the training pant periphery by suitable attachment mechanisms (not shown) such as adhesive bonds, ultrasonic (sonic) bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the bodyside liner to the outer cover. It should be readily appreciated that the above-described attachment means may also be employed to suitably interconnect, assemble and/or affix together the various other component parts of the articles which are described herein.

As previously described, the absorbent body structure is positioned between the outer cover and the bodyside liner. The absorbent body structure can be any structure or combination of components which are generally compressible, conformable, non-irritating to a wearer's skin, and capable of absorbing and retaining liquids and certain body wastes. For example, the structure may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One desirable type of fluff is identified with the trade designation CR 1654, available from U.S. Alliance of Childersburg, Ala., USA, and is a bleached, highly absorbent sulfate wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.10 to about 0.35 grams or higher per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 10 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable tissue wrap that aids in maintaining the integrity and shape of the absorbent structure.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or nonwoody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

In the practice of the current invention, higher performance, elastomeric materials are combined with relatively lower performance elastomeric, stretchable, or plastomer materials in an article outercover, in order to economically provide full circumferential stretch in garments over a wide range of consumer sizes. While normally relatively low performance elastomeric materials, such as materials having high tension, high permanent set, and poor stretch recovery after an initial extension, may be used with a garment that is tailored to fit a specific narrow size range, acceptable elastomeric performance over a large size range can be achieved if this same material is coupled with a relatively higher performance elastomeric material, that is one that demonstrates relatively lower tension, lower permanent set, and improved stretch recovery (as measured by hysteresis), when compared to the low performance elastomeric material, stretchable material or plastomer under similar test conditions.

An article of the present invention is designed to deliver full circumferential stretch around the entire body of the consumer. The stretch is sufficient to fit consumers of varying sizes at the waist, hip and leg areas, as well as to accommodate the typical over-extension at the waist and around the legs by consumer, during the donning process. The stretch is designed to be progressive in at least three locations on the article, in that the level of stretchability (or elastomeric performance) progressively increases as one travels from the crotch area, and proximate front and back waist areas, to each of the two side panel areas and the waistband area. The product also delivers continued elastomeric and/or stretch functionality during dynamic use (that is continuing regular stretching and retraction associated with normal use) in order to maintain the fit and minimize droop or sagging during such use.

In a first embodiment of the invention of FIG. 1, the crotch area (zone) 26 desirably includes stretchable materials and more desirably elastomeric materials which demonstrate relatively high hysteresis and permanent set values determined by the Extension/retraction Test described. These values are relatively high compared to other zones within the article outercover.

This zone also desirably demonstrates high to low stretch to stop values as determined by the Stretch to Stop test and desirably provides a moisture barrier and low to moderate breathability as determined by a WVTR test Desirably, in one embodiment, the value of hysteresis for materials making up the outercover crotch area (zone) which also may include areas proximate to the crotch, such as the front and back waist areas (excluding the waist band areas such as 28 and 30), as measured in percent (%), is between about 5 and 85. Desirably in one embodiment, the value of stretch to stop for material making up the outercover crotch area, as measured in percent (%), is between about 0 and 250. Finally, it is desirable in one embodiment that the WVTR value, as measure in grams per square meter for 24 hours be between about 0 and 2000.

In contrast, the side panels or side areas (zones) of the outercover which are positioned over a user's hip areas (such as in the side seam area, or refastenable panel area), whether they be the side areas of a single piece article, or separately formed side panels (either bonded or refastenable), desirably demonstrate the attributes of low to moderate hysteresis for the side material, as determined by the Extension/retraction test, (low to moderate permanent set for the side material, higher stretch to stop for the side material relative to the crotch zone, as determined by the Stretch-to-stop test, and higher breathability for the side material, as determined by the WVTR test, when compared to the crotch zone values.

Desirably, in one embodiment, the value of hysteresis, as measured in %, is between about 0 and 60. Desirably, in one embodiment, the value of stretch to stop, as measured in %, is between about 100 and 300. Finally, it is desirable that in one embodiment, the WVTR value, as measure in grams per square meter for 24 hours be between about 600 and 5000.

Desirably, in one embodiment, the article of FIG. 1 also includes a fourth progressively stretchable zone in the waistband area having the following elastic properties. Such an elastic waistband may be discrete as shown (in that it encompasses only a portion of the waist area encircling the waist opening), or may be continuous around the entire circumference of the waist opening. Such a waistband desirably demonstrates low hysteresis with respect to at least the crotch zone (actually low hysteresis and permanent set), and higher stretch to stop than the crotch area as well, as determined by the Stretch-to-stop Test.

Desirably, in one embodiment, the value of hysteresis of the waistband zone, as measured in %, is between about 0 and 60. Desirably, in one embodiment the value of stretch to stop of the waist band zone, as measured in percent (%), is between about 100 and 300.

An article produced in accordance with the invention may have at least a three zone design for a stretchable or elastomeric outercover, and is desirably used along with a stretchable liner and a stretchable absorbent body structure.

In such a product, the properties of stretchable or elastomeric side panels, or side areas of the outercover over the hips, encompass two of the elastomeric zones and the remainder of the stretchable outercover in the crotch area encompasses a third elastomeric zone. Each are synergistically interactive. Such an article desirably includes a higher performance elastomeric material in the side panels or side areas of the outer cover, and includes lower performance elastomeric material, stretchable material (or plastomers) in the remainder of the outer cover, with the exception of the waistband areas.

In particular, as can be seen in FIG. 1, a first type of elastomeric material may be placed in the areas/zone designated as 50 and 52, and a second elastomeric component, stretchable component or plastomer material may be placed in the areas/zone designated by 54.

An example of a material that may be used as the higher performance elastomer component of the side panels or sides of the outercover includes stretch bonded laminate produced in accordance with a continuous stretch bonded laminate process utilizing an elastic filament array and meltblown web laminate, as described in U.S. Pat. No. 5,385,775 which is hereby incorporated by reference in its entirety. Alternatively, such a stretch bonded laminate may be produced using a filamentary array without a nonwoven web complement. Still in a further alternative embodiment of the present invention, a film or a nonwoven web stretch bonded laminate may be utilized. In either event, each of the laminates is produced in such a way that the array, film or nonwoven web is stretched before being bonded to a gatherable layer. The gatherable layer and elastic component are then allowed to retract, creating an elastic laminate with desired stretch attributes. The laminate may typically stretch to the extent that the gatherable layer becomes ungathered.

Figure 3:
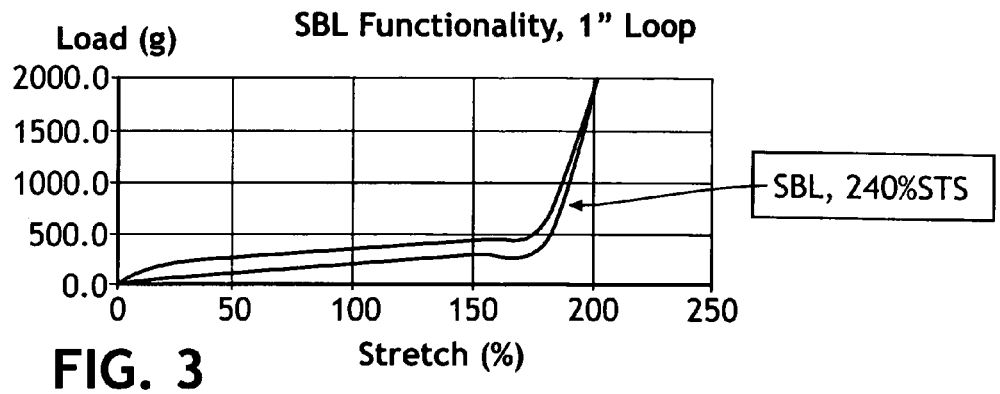
FIG. 3 represents a stress strain curve of a stretch bonded laminate (SBL) material made from a higher performance elastomeric material.

An exemplary stretch bonded laminate structure such as that described in U.S. Pat. No. 5,385,775 and including a stretch to stop value of approximately 240%, was tested for its elastic attributes and the results are reflected in FIG. 3, which illustrates a stress/strain (stretch/relaxation) curve for a one inch wide sample of the above described stretch bonded laminate material tested using the extension/retraction test described. In particular, the laminate included a lamination of an array of continuous filaments and meltblown layers of a styrenic block copolymer (Kraton G2740), and two gatherable layers of polypropylene spunbond. The spunbond may be between about 0.3 and 0.6 osy per layer (was about 0.4 osy in the example) and the array/meltblown elastomeric portion may be between 15 and 20 gsm (in the example was about 18.5 gsm) basis weight. The retracted laminate basis weight at 150% stretch to stop is about 3.36 osy when gathered. As can be seen from the graph, the material demonstrates high stretch (up to 200 percent of its original length), relatively low and uniform tension across its stretched length, low permanent set (relaxation curve returns to zero near its initial starting point) and minimum loss between the stretch and relaxation curves. This loss, measured as the percent difference between the areas under each curve, is a measure of the hysteresis and in this case is about 40 percent. The second measure of functionality loss (permanent set) is about 5 percent.

An exemplary material for use in the central stretch area (or crotch zone) adjacent the side panels/or outercover side areas, is a neck bonded laminate, and in particular, a single site catalyzed neck bonded laminate material. By single site catalyzed neck bonded laminate is meant that at least one of the layers in the laminate is comprised of a single site catalyzed material. Such single site catalyzed materials could include catalyzed polyolefins, e.g., ethylene, propylene, or other olefinic molecules. The polyolefins may desirably have a density from about 0.80 to 0.95 grams/cubic centimeter (g/cc) and desirably under 0.90 grams/cc, according to some aspects of the invention.

Single site catalyzed polyolefins are particularly useful as the elastomeric portion of the necked bonded laminate. Such materials are perhaps better characterized as plastomers rather than elastomers, since they include qualities of both plastic and elastomeric materials. Single site catalyzed polyolefins that are useful include those described in U.S. Pat. Nos. 5,571,619, 5,322,728, and 5,272,236 the disclosures of which are incorporated herein by reference.

Polymers made using single site catalysts have a very narrow molecular weight range. Polydispersity numbers ($M_W/M_N$) of below 4 and even below 2 are possible for metallocene-produced polymers. These polymers also have a controlled short chain branching distribution compared to otherwise similar Ziegler-Natta produced type polymers. It is also possible using single site catalyst systems to control the isotacticity of the polymer quite closely.

Single site catalyzed polymers are available from Exxon-Mobil Chemical Company of Baytown, Tex. under the trade name ACHIEVE for polypropylene based polymers and EXACT and EXCEED for polyethylene based polymers. Dow Chemical Company of Midland, Mich. has polymers commercially available under the names ENGAGE and AFFINITY. These materials are believed to be produced using non-stereo selective single site catalysts. Exxon-Mobil generally refers to their single site catalyst technology as "metallocene" catalysts, while Dow refers to theirs as "constrained geometry" catalysts to distinguish them from traditional Ziegler-Natta catalysts which have multiple reaction sites. Other manufacturers such as Fina Oil, BASF, Amoco, Hoechst and Mobil are active in this area as well.

For the purposes of the testing, the metallocene-catalyzed necked bonded laminate included two facings of approximately 0.5 osy polypropylene spunbond (17 g/m2, polypropylene spunbond fabric) with wire weave pattern bonding, and a core film layer of a metallocene-catalyzed material from Dow XU 58380 (10 ml in thickness) and including approximately 4 percent Titanium dioxide for coloring. The core basis weight of the film ranged from about 20-30 gsm, and the facing neck stretching ranged from about 45 to 60 percent. The mNBL had an extendibility and stretchability along the necked-gathering direction of the composite.

Figure 4:
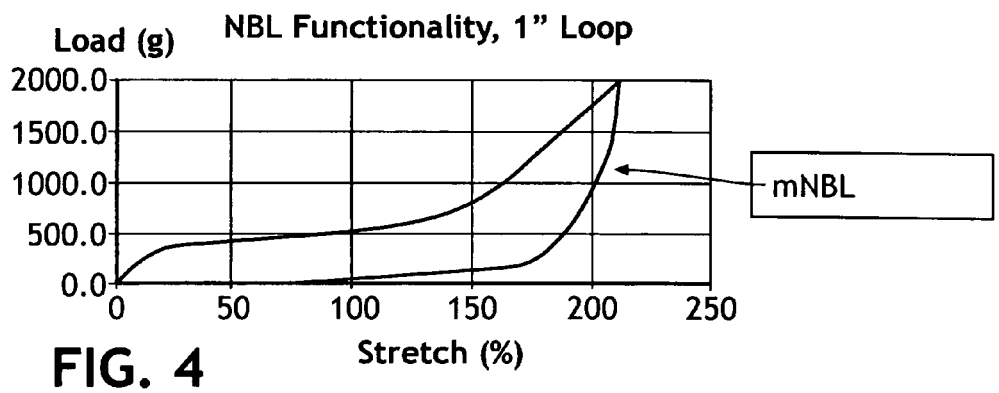
FIG. 4 represents a stress strain curve of a necked bonded laminate material (NBL) made from a lower performance elastomeric or plastomer material.

The comparable stress/strain curve of such neck bonded laminates (a one inch wide sample), including a single-site catalyzed layer can be seen in FIG. 4. As seen in FIG. 4, such materials demonstrate initially high stretch (in excess of 200 percent), but lower performing hysteresis characteristics (76 percent loss of area) and higher permanent set (84 percent of the original sample length). Tension at 25 percent stretch extension was about 360 g and on the retraction cycle at 25 percent was about 0 g (due to set). Tension at 150 percent stretch extension, however, was about 800 g but only 150 g on the retraction cycle at 150 percent.

For reference, the higher performance stretch bonded laminate material (FIG. 3) also has a high initial stretch (200 percent), with lower hysteresis characteristics (about 36 percent loss of area) and lower permanent set of about 20 percent of the original sample length. Tension at 25 percent stretch extension was about 250 g and on the retraction cycle at 25 percent was about 60 g. Tension at 150 percent stretch extension, however, was about 425 g and 290 g on the retraction cycle at 150 percent.

Other materials that may be used in the various zones (and in particular the crotch zone) include extensible materials formed from laminates that have been pre-strained.

Suitable elastic materials, as well as one described process of incorporating elastic side panels into a training pant, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material include a stretch-thermal laminate (STL) or a reversibly necked laminate. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al., all of which are incorporated herein by reference. Alternatively, the side panel material may include other woven or nonwoven materials.

The three zone outercover structure combines attributes of both of these materials to make them synergistically interactive. In this fashion, side panels provide initial stretch for the over-extending that accompanies donning, dynamic use and fit maintenance, while the lower performance elastomeric material, stretchable material or plastomer material provides additional initial stretch for donning and sizing of variously shaped consumer, and synergistic interaction with the side panel material in order to maintain the dynamic fit during use, as well as minimal distortion of graphics on the outer cover during use.

Figure 5:
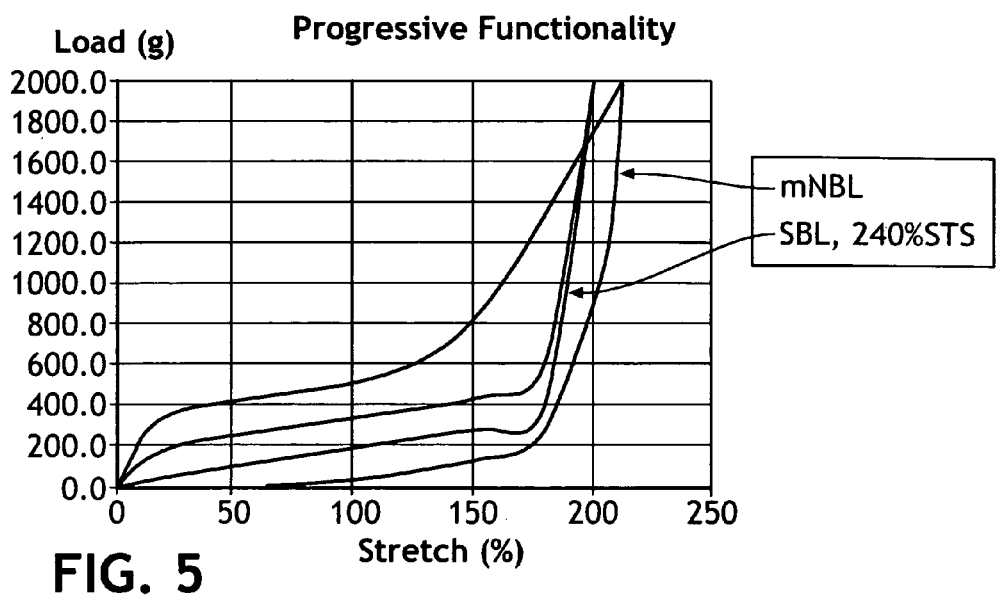
FIG. 5 represents a stress strain curve of the previously described two materials superimposed, one over the other, demonstrating that many of the stretch bonded laminate material performance attributes fall within the necked bonded laminate material performance attributes.

In order to effectively synergize the two material components of the article, it has been discovered that the stress/strain curves of the higher performance elastomeric side panel material should desirably lie within the stress/strain curves of the remainder crotch zone outercover material as seen in FIG. 5. By requiring the material attributes to be combined in this fashion, the side panel or side seam areas of the article are first stressed during product use, prior to stressing the central outercover materials. This allows for almost full retraction of the side panels to properly fit the consumer, before the central outercover portion/zone is compromised by its higher hysteresis or permanent set attributes. Desirably, in one embodiment such first zones on the sides (side panel) of the outercover, demonstrate a hysteresis value between about 0 and 60, and a tension at 30% elongation lower than in the $2^{nd}$ crotch zone. Desirably, such second zone in the crotch area of the outercover of the article demonstrates a hysteresis value between about 40 and 100, and a tension at 30% elongation higher than zone 1 (side panels).

EXAMPLES

In a hypothetical example of an article taking advantage of the progressive stretch functionality, using the performance curves of FIG. 5, a 400 gram load/force applied to an article of the type described, that is one that includes a progressive stretch outercover with stretch-bonded laminate side panels and stretch neck-bonded laminate, on the remaining portion of the outercover would cause the side panels to stretch about 130 percent, while the necked bonded laminate outercover portion could stretch only about 30 percent. Dynamic, in use fit would be provided by the stretch bonded laminate, since the necked bonded laminate would only contribute about 7 percent due to hysteresis effects (30 percent stretch×(100 percent total−77 percent loss)=6.9 percent).

If however, in a second hypothetical example, an 800 gram load were applied to fit a larger child, or individual, the stretch bonded laminate would initially contribute about 180 percent, while the neck bonded laminate would initially contribute about 150 percent. Most of the dynamic, in use fit would still be provided by the stretch bonded laminate, since the neck bonded laminate would only contribute about 34 percent due to the hysteresis effects (150 percent stretch−(100 percent total−77 percent loss)=34 percent). The difference between the two examples is the consumer size, where the materials used to don and fit a smaller individual in Example 1 are also used to don and fit a much larger individual in Example 2. The only thing that changes is the effective use of the necked bonded laminate in extending the donning size range while maintaining a reasonable dynamic fit range.

A third hypothetical example of the synergistic effects of the inventive outercovers is illustrated in Table 1 which follows. Sizing of a hypothetical training pant is calculated with 120 mm wide side panels and a 230 mm outer cover (between side panels) of a 350 mm initial waist size. The calculations assume that a minimum of 50 grams load is necessary to maintain dynamic fit. Therefore, permanent set at a 50 gram loading level becomes the threshold level for functional stretch. Based on FIG. 5, these values are about 10 percent, (20 percent/200 percent) for the stretch bonded laminate material and about 55 percent (120 percent/220 percent) for the neck bonded laminate material. A comparison is drawn between the performance expected from a stretchbonded laminate and neck bonded laminate combination versus just a neck bonded laminate material for an outercover.

such a situation, the article includes a complete elastic waist band zone in addition to the side panel and outercover zones. For instance, a high performance waist band, having high stretch, low hysteresis and low set is utilized to completely encircle the waist opening. The waist band elastic functionality provides the basis for ease of donning and fit maintenance. The side panels are in turn composed of lower performance elastic materials (lower stretch, higher hysteresis/set).

The central elastic zone in the crotch area is a stretchable composite that has even less effective stretch (stretch to stop), more hysteresis, and/or more set. The areas of the article requiring a large amount of stretch that must be held under tension in use, for an extended period of time (such as the hip areas) can be constructed with low hysteresis materials. Likewise, the areas of the article that are only stretched when the article is being donned, can be constructed of higher hysteresis materials. The higher elastic hysteresis materials ensure that the stretch in the central portion will be utilized only as the garment is donned or only on the largest individuals, thus reducing the impact of its negative characteristics. This combination allows for gradients in both the longitudinal and lateral directions.

For instance, in the vertical direction, a gradient is formed between the waist band zone at the top of the stretchable outer cover structure. The waist band provides for most of the elastic fit performance of the article. In contrast, the outercover need only conform to the body. There is additionally a horizontal/lateral elastic property gradient of this article, as the side panel materials are used to provide a comfortable fit

TABLE 1

Waist Dimensions of Hypothetical Article

| Materials | Loading (g) | Initial Size (mm) | Increase due to loading SBL | Increase due to loading NBL | Increase after hysteresis SBL | Increase after hysteresis NBL | Donning Size (mm) | Dynamic Fit Range (mm) |
|---|---|---|---|---|---|---|---|---|
| | 400 | 350 | 130% | 30% | 10% | 55% | | |
| SBL/NBL | | | 156 | 69 | 16 | 38 | 575 | 404-575 |
| NBL only | | | 0 | 105 | 0 | 58 | 455 | 408-455 |
| | 800 | 350 | 180% | 150% | 10% | 55% | | |
| SBL/NBL | | | 216 | 345 | 22 | 190 | 911 | 562-911 |
| NBL only | | | 0 | 525 | 0 | 289 | 875 | 639-875 |

As can be seen from the above table, the use of a stretch-bonded laminate and neck bonded laminate combination (SBL/NBL) extends the donning size and fit range, for both smaller and larger individuals and, in fact, allows a better fit across a wider range of sizes in general. The SBL/NBL combination functions across a range of 404 mm to 911 mm with a dynamic fit range of at least 171 mm. The NBL alone, in comparison, as a stretchable material, would fit across a similar range, but would have much less dynamic fit (only 47 mm at the lower end), suffering from permanent set and hysteresis performance. The synergistic use of both materials efficiently and economically provides sufficient range for dynamic fit and sufficient stretch for over-extension during donning.

In an alternative embodiment composites of elastic and plastic deformable materials can be utilized to optimize article functionality in both horizontal and vertical gradients in an article outercover. In a first example of an alternate embodiment, the outercover benefits from three different elastic zones (in four locations on the article outer cover) rather than the two different elastic zones in three different locations on the article outercover as previously described. In over time, as well as ease of donning. Since the side panels are in a stretched out/under tension condition while worn in an article, they should be made of low hysteresis materials. The outercover/and liner structure of the article in the center crotch area of the article, is only under significant tension while the article is stretched to the maximum as it is donned. Therefore it can be constructed of materials with high hysteresis. It should be recognized, that as the donned article stretches either during donning or during continued use, the stretched areas of the central elastic zone would become more breathable, as such materials include layers that are filled with particles.

Since the outercover will become more breathable in the highly stretched areas, it would in effect have areas of highly zoned breathability as well in those areas. These highly stretched areas, would therefore provide higher breathability where it is needed most, such as around the hip areas.

In one embodiment, it is desirable that such a three separate zone gradient (of four locations) demonstrate the following properties as described in Table 2.

TABLE 2

| Properties | Waistband Zone | Side Panel Zone | Central Crotch Zone |
|---|---|---|---|
| Stretch to Stop | 125-250% | 125-250% | 0-250% |
| Hysteresis | <60% | <60% | <85% |
| Set | <10% | <10% | <35% |
| Breathability | N.A. | >600 WVTR but des. >1500 WVTR or higher | >600 WVTR but des. >1500 WVTR |
| Hydro-head | N.A. | N.A. | >60 in. water |

In an alternate embodiment, an absorbent article includes a stretchable outercover layer, a liner layer, and an absorbent layer contained between the stretchable outercover layer and the liner layer, the absorbent article having a longitudinal direction and longitudinal ends, and a lateral direction and lateral sides. The article further includes a front waist region at a first longitudinal end, a back waist region at an opposite longitudinal end, and a crotch region extending longitudinally between the front and back waist regions. Laterally extending ear portions are defined at opposed lateral sides of the front and back waist regions. The outercover includes at least three material zones, with a first zone situated in the crotch region between the front waist region and the back waist region and demonstrating a level of hysteresis of between about 5 and 85 percent. Second and third zones are situated on the laterally extending ear portions of the outercover and demonstrate a level of hysteresis of between about 0 and 60 percent. In an alternative embodiment, the absorbent article includes a fourth zone situated at the front and back waist regions. The fourth zone demonstrates a level of hysteresis of between about 0 and 60 percent.

In a further alternative embodiment, an absorbent garment includes an absorbent chassis defining a waist opening and first and second leg openings; the absorbent chassis having a front region, a crotch region, and a back region, with two side panels each joining the front region and the back region, each of the side panels including a front panel and a back panel attached to one another along a side seam with an elastic waistband structure attached to the waist opening edge. The front, back and crotch regions are covered by an outer cover and the outer cover has a hysteresis of greater than or equal to 40% and a tension at 25% elongation (on a first extension cycle) of 300 g or more. The side panels have a hysteresis of less than or equal to 60% and a tension at 25% elongation (on the first extension cycle) of 100 g or more. The side waistband has a hysteresis of less than or equal to 60% and a tension at 25% elongation (on a first extension cycle) of 100 g or more.

In an alternative embodiment, the absorbent garment outer cover demonstrates a percent set of greater than 50%. In still a further alternative embodiment, the absorbent garment side panels demonstrate a percent set of less than 15%. In still a further alternative embodiment, the absorbent garment outer cover demonstrates a WVTR of greater than 3000 g per square meter for 24 hours. In still a further alternative embodiment, the absorbent garment side panels demonstrate a WVTR of greater than 600 g per square meter for 24 hours. In still a further alternative embodiment, the absorbent garment outer cover demonstrates a tension at 150% elongation of less than 2000 g. In still a further alternative embodiment, the absorbent garment side panels demonstrate a tension at 150% elongation of less than 600 g.

In still a further alternative embodiment, an absorbent garment includes an absorbent chassis defining a waist opening and first and second leg openings; the absorbent chassis having a front region, a crotch region, and a back region, with two side panels each joining the front region and the back region, each of the side panels including a front panel and a back panel attached to one another along a side seam with an elastic waistband structure attached to the waist opening edge. The front, back and crotch regions are covered by an outer cover and the outer cover has a hysteresis of greater than or equal to 80% and a tension at 25% elongation (on a first extension cycle) of 400 g or more. The side panels have a hysteresis of less than or equal to 40% and a tension at 25% elongation (on a first extension cycle) of 200 g or more. The side waistband has a hysteresis of less than or equal to 40% and a tension at 25% elongation (on a first extension cycle) of 200 g or more.

In an alternative embodiment, the absorbent garment outer cover demonstrates a percent set of greater than 80%. In still a further alternate embodiment, the absorbent garment side panels demonstrate a percent set of less than 10%. In still a further alternate embodiment, the absorbent garment outer cover demonstrates a WVTR of greater than 1500 g per square meter for 24 hours. In still a further alternate embodiment, the absorbent garment side panels demonstrate a WVTR of greater than 1500 g per square meter for 24 hours. In still a further alternate embodiment, the absorbent garment outer cover demonstrates a tension at 150% elongation of less than 1800 g. In still a further alternate embodiment, the absorbent garment side panels demonstrate a tension at 150% elongation of less than 500 g.

In still a further alternative embodiment an absorbent garment includes an absorbent chassis defining a waist opening and first and second leg openings; the absorbent chassis having a front region, a crotch region, and a back region, with two side panels each joining the front region and the back region, each of the side panels including a front panel and a back panel attached to one another along a side seam with an elastic waistband structure attached to the waist opening edge. The front, back and crotch regions are covered by an outer cover and the outer cover has a hysteresis of between about 80% and 100% and a tension at 25% elongation (on a first extension cycle) of 500 g or more. The side panels have a hysteresis of less than or equal to 20% and a tension at 25% elongation (on a first extension cycle) of 250 g or more. The side waistband has a hysteresis of less than or equal to 20% and a tension at 25% elongation (on a first extension cycle) of 250 g or more.

In an alternative embodiment, the absorbent garment outer cover demonstrates a percent set of up to 100%. In still a further alternative embodiment, the absorbent garment side panels demonstrate a percent set of less than 5%. In still a further alternative embodiment, the absorbent garment outer cover demonstrates a WVTR of greater than 600 g per square meter for 24 hours. In still a further alternative embodiment, the absorbent garment side panels demonstrate a WVTR of greater than 3000 g per square meter for 24 hours. In still a further alternative embodiment, the absorbent garment outer cover demonstrates a tension at 150% elongation of less than 1500 g. In still a further alternative embodiment, the absorbent garment side panels demonstrate a tension at 150% elongation of less than 400 g.

While in the previous embodiment, the different zones making up the stretch gradient comprise a variety of materials, in an alternative embodiment, the stretch outercover does not include different materials, but is instead made from one sheet of material that has instead been treated in different ways during the manufacturing process. For instance, adhesive sprays can be used to inhibit stretch in certain areas by attaching the outercover to materials with different elastic properties, thus causing an elastic property gradient. For instance, if in the previous embodiments, the absorbent structural component is in a floating unattached from in the article chassis between an elastic liner and an elastic or stretchable outercover, it may be attached to the outercover in various locations to limit stretch functionality in those select areas. Furthermore, sprays of adhesives or other materials may be used to create additional gradients of breathability as they would block pores that may be contained in the various layers.

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. An absorbent article comprising a stretchable outercover layer, a stretchable liner layer, and an absorbent layer contained between said stretchable outercover layer and said stretchable liner layer, said absorbent article having a longitudinal direction and longitudinal ends, and a lateral direction and lateral sides, said article further comprising
   a front waist region at a first longitudinal end, a back waist region at an opposite longitudinal end, and a crotch region extending longitudinally between said front and back waist regions;
   laterally extending ear portions defined at opposed lateral sides of said front and back waist regions,
   wherein said outercover includes at least three material zones, with a first zone situated in the crotch region between the front waist region and the back waist region and demonstrating a higher level of hysteresis than a second and third zone of between about 5 and 85 percent, with second and third zones situated on the laterally extending ear portions of said outercover and demonstrating a level of hysteresis of between about 0 and 60 percent;
   wherein said second and third zones of said outercover comprise a higher performance elastomeric material than the elastomeric material of said first zone;
   wherein said elastomeric material of said second and third zones and said elastomeric material of said first zone are synergistically interactive.

2. The absorbent article of claim 1 wherein said article includes a fourth zone situated at the front and back waist regions, said fourth zone demonstrating a level of hysteresis of between about 0 and 60 percent.

3. An absorbent garment, comprising:
   an absorbent chassis defining a waist opening and first and second leg openings;
   the absorbent chassis having a front region, a crotch region, and a back region, with two side panels each joining the front region and the back region, each of the side panels including a front panel and a back panel attached to one another along a side seam with an elastic waistband structure attached to said waist opening edge;
   wherein said front, back and crotch regions are covered by an outer cover and said outer cover has a higher hysteresis than said side panels of greater than or equal to 40% and a tension at 25% elongation (on a first extension cycle) of 300 g or more;
   wherein said side panels have a hysteresis of less than or equal to 60% and a tension at 25% elongation (on a first extension cycle) of 100 g or more; wherein said side waistband has a hysteresis of less than or equal to 60% and a tension at 25% elongation (on a first extension cycle) of 100 g or more;
   wherein said side panels comprise a higher performance elastomeric material than the elastomeric material of said front, back, and crotch regions;
   wherein said elastomeric material of said side panels and said elastomeric material of said front, back, and crotch regions are synergistically interactive.

4. The absorbent garment of claim 3 wherein said outer cover demonstrates a percent set of greater than 50%.

5. The absorbent garment of claim 3 wherein said side panels demonstrate a percent set of less than 15%.

6. The absorbent garment of claim 3 wherein said outer cover demonstrates a water vapor transmission rate (WVTR) of greater than 3000 g per square meter for 24 hours.

7. The absorbent garment of claim 3 wherein said side panels demonstrate a WVTR of greater than 600 g per square meter for 24 hours.

8. The absorbent garment of claim 3 wherein said outer cover demonstrates a tension at 150% elongation of less than 2000 g.

9. The absorbent garment of claim 3 wherein said side panels demonstrate a tension at 150% elongation of less than 600 g.

10. An absorbent garment, comprising:
    an absorbent chassis defining a waist opening and first and second leg openings;
    the absorbent chassis having a front region, a crotch region, and a back region, with two side panels each joining the front region and the back region, each of the side panels including a front panel and a back panel attached to one another along a side seam with an elastic waistband structure attached to said waist opening edge;
    wherein said front, back and crotch regions are covered by an outer cover and said outer cover has a hysteresis of greater than or equal to 80% and a tension at 25% elongation (on a first extension cycle) of 400 g or more;
    wherein said side panels have a hysteresis of less than or equal to 40% and a tension at 25% elongation (on a first extension cycle) of 200 g or more;
    wherein said side panels comprise a higher performance elastomeric material than the elastomeric material of said front, back, and crotch regions;
    wherein said elastomeric material of said side panels and said elastomeric material of said front, back, and crotch regions are synergistically interactive;
    wherein said side waistband has a hysteresis of less than or equal to 40% and a tension at 25% elongation (on a first extension cycle) of 200 g or more.

11. The absorbent garment of claim 10 wherein said outer cover demonstrates a percent set of greater than 80%.

12. The absorbent garment of claim 10 wherein said side panels demonstrate a percent set of less than 10%.

13. The absorbent garment of claim 10 wherein said outer cover demonstrates a WVTR of greater than 1500 g per square meter for 24 hours.

14. The absorbent garment of claim 10 wherein said side panels demonstrate a WVTR of greater than 1500 g per square meter for 24 hours.

15. The absorbent garment of claim 10 wherein said outer cover demonstrates a tension at 150% elongation of less than 1800 g.

16. The absorbent garment of claim 10 wherein said side panels demonstrate a tension at 150% elongation of less than 500 g.

17. An absorbent garment, comprising:
    an absorbent chassis defining a waist opening and first and second leg openings;
    the absorbent chassis having a front region, a crotch region, and a back region, with two side panels each joining the front region and the back region, each of the side panels including a front panel and a back panel attached to one another along a side seam with an elastic waistband structure attached to said waist opening edge;

wherein said front, back and crotch regions are covered by an outer cover and said outer cover has a hysteresis of between about 80% and 100% and a tension at 25% elongation (on a first extension cycle) of 500 g or more;

wherein said side panels have a hysteresis of less than or equal to 20% and a tension at 25% elongation (on a first extension cycle) of 250 g or more;

wherein said side panels comprise a higher performance elastomeric material than the elastomeric material of said front, back, and crotch regions;

wherein said elastomeric material of said side panels and said elastomeric material of said front, back, and crotch regions are synergistically interactive;

wherein said side waistband has a hysteresis of less than or equal to 20% and a tension at 25% elongation (on a first extension cycle) of 250 g or more.

18. The absorbent garment of claim 17 wherein said outer cover demonstrates a percent set of up to 100%.

19. The absorbent garment of claim 17 wherein said side panels demonstrate a percent set of less than 5%.

20. The absorbent garment of claim 17 wherein said outer cover demonstrates a WVTR of greater than 600 g per square meter for 24 hours.

21. The absorbent garment of claim 17 wherein said side panels demonstrate a WVTR of greater than 3000 g per square meter for 24 hours.

22. The absorbent garment of claim 17 wherein said outer cover demonstrates a tension at 150% elongation of less than 1500 g.

23. The absorbent garment of claim 17 wherein said side panels demonstrate a tension at 150% elongation of less than 400 g.

* * * * *